United States Patent
Marzi et al.

(10) Patent No.: US 7,273,873 B2
(45) Date of Patent: Sep. 25, 2007

(54) CAMPTOTHECINS WITH A MODIFIED LACTONE RING

(75) Inventors: Mauro Marzi, Rome (IT); Elena Marastoni, Rome (IT); Claudio Pisano, Rome (IT); Maria Ornella Tinti, Rome (IT); Cabri Walter, Rome (IT); Alpegiani Marco, Milan (IT); Vergani Domenico, Rome (IT); Danelli Tamara, Rome (IT); Gomez Patricio Martin, Rome (IT); Vesci Loredana, Rome (IT); Zunino Franco, Milan (IT); Penco Sergio, Rome (IT)

(73) Assignees: Sigma-Tau Industrie Farmaceutiche Riunite S.p.A., Rome (IT); Instituto Nazionale per Lo Studio e La Cura Dei Tumori, Milan (IT)

( * ) Notice: Subject to any disclaimer, the term of this patent is extended or adjusted under 35 U.S.C. 154(b) by 0 days.

(21) Appl. No.: 10/511,724

(22) PCT Filed: May 28, 2003

(86) PCT No.: PCT/IT03/00328

§ 371 (c)(1),
(2), (4) Date: Oct. 19, 2004

(87) PCT Pub. No.: WO03/101995

PCT Pub. Date: Dec. 11, 2003

(65) Prior Publication Data

US 2005/0154003 A1    Jul. 14, 2005

(30) Foreign Application Priority Data

May 31, 2002    (IT)    ................... RM2002A0305

(51) Int. Cl.
*A61K 31/4745*    (2006.01)
*C07D 491/22*    (2006.01)
(52) U.S. Cl. ........................................ 514/283; 546/48
(58) Field of Classification Search ................ 514/283; 546/48
See application file for complete search history.

(56) References Cited

U.S. PATENT DOCUMENTS

| 4,399,276 A | * | 8/1983 | Miyasaka et al. | ............ 544/361 |
| 6,242,457 B1 | * | 6/2001 | Penco et al. | ................. 514/283 |
| 2001/0008939 A1 | | 7/2001 | Lucio et al. | |

FOREIGN PATENT DOCUMENTS

| EP | 1 044 977 | 10/2000 |
| WO | WO97/00876 | 1/1997 |

OTHER PUBLICATIONS

Bom, D., et al., " Novel A, B, E-Ring-Modified Comptothecins Displaying High Lipophilicity and Markedly Improved Human Blood Stabilities", *J. Med. Chem.*, 42:3018-3022 (1999).
Dallavalle, S., et al., "Perspectives in camptothecin development", *Expert Opin. Ther. Patents*, 12(6):837-844 (2002).
Hertzberg, R.P., et al., "Modification of the Hydroxy Lactone Ring of Camptothecin: Inhibition of Mammalian Topoisomerase I and Biological Activity", *J. Med. Chem.*, 32:715-720 (1989).

* cited by examiner

*Primary Examiner*—Charanjit S. Aulakh
(74) *Attorney, Agent, or Firm*—Nixon & Vanderhye P.C.

(57) ABSTRACT

Compounds of formula (I) or (II) are described: where the groups are as defined in the description here below, the racemic mixtures, their individual enantiomers, their individual diastereoisomers, their mixtures, and their pharmaceutically acceptable salts. Said compounds are topoisomerase I inhibitors.

6 Claims, No Drawings

CAMPTOTHECINS WITH A MODIFIED LACTONE RING

This application is the U.S. National Phase of International Application PCT/IT03/00328, filed on May 28, 2003, which designated the U.S. and claims priority to Italian Application No. RM 2002A000305, filed May 31, 2002. The entire contents of these applications are incorporated herein by reference.

The invention described herein relates to compounds useful as medicaments, particularly derivatives of camptothecin with structural modifications of the lactone ring, to processes for their preparation, to their use as active agents endowed with topoisomerase I inhibiting activity and to pharmaceutical compositions containing them as active ingredients.

BACKGROUND TO THE INVENTION

Camptothecin is an alkaloid isolated by Wall et al. (*J. Am. Chem. Soc.*, 88, 3888-3890 (1966)) for the first time from the tree *Camptotheca acuminata*, a plant native to China, belonging to the Nyssaceae family. The molecule consists of a pentacyclic structure with a lactone in the E ring, which is essential for cytotoxicity.

For a review of the camptothecins and the problems relating to their use as medicaments, as well as the resolution of a number of such problems, see European Patent EP 1044977, filed in the name of the applicant.

As regards the problem of the lactone ring, which is a portion of the molecule essential for the camptothecins to be able to exercise their pharmacological activity, one aspect which has yet to be fully resolved is the stability of the ring itself, which, in turn, is responsible for the half-life of the drug.

Patent application WO 97/00876, filed in the name of Societè de Conseils de Recherches et d'Applications Scientifiques, and published on Jan. 9, 1997, describes camptothecins in which the lactone ring has been modified from its original α-hydroxylactone structure to a β-hydroxylactone structure (homocamptothecins), bringing the lactone cycle up from six to seven members. These compounds inhibit topo-isomerase I DNA relaxation activity and are endowed with cytotoxic activity against several tumour lines. The β-hydroxylactone structure is defined as a lactone that involves the presence of a supplementary carbon atom between the carboxyl carbon atom and the carbon atom in α-bearing the hydroxy in the α-hydroxylactone structure. To increase the stability of the lactone ring, the inventors suggest substituents on the supplementary carbon atom, and the substituents indicated are the lower alkyls together with the lower alkoxy, halogen or hydroxy. In the patent application mentioned no evidence of improved stability of the lactone ring is provided. In a subsequent patent application, WO 98/28304, published on Jul. 2, 1998, the same applicant describes further camptothecins with a β-hydroxylactone structure, where the hydroxy group is functionalised with groups that are capable of restoring it in vivo, thus effectively furnishing prodrugs of the molecules described in the preceding patent application, and also resolving the problem of the severe side effects of products in the present state of the art. In this case, too, no experimental evidence is provided that the technical problem has been solved. In *J. Med. Chem.*, 1998, Vol 41, No 27, 5410-5419, the same inventors as in the abovementioned patent applications indicate the lactone in position 7, therein described, as an instrument for increasing the stability of the lactone ring, and thus as a useful model for elaborating further camptothecin derivatives. See also *Bioorg. Med. Chem. Lett.*, 9, (1999) 2599-2602; *Biochemistry*, 1999, 38, 15556-15563; *Cancer Research*, 59 2939-2943. Other modifications of homocamptothecin on the A and B rings are described in WO 00/61146, University of Pittsburgh et al., published on Oct. 19, 2000, and in *J. Med. Chem.*, 1999, 42, 3018-3022 for the so-called "homosilatecans", which are potent, stable topo-isomerase I inhibitors. Homocamptothecins with further modifications are described in *J. Med. Chem.*, 2000, 43, 2285-2289, *Anti-cancer Drug Design*, (2001), 12, 9-19, where the anticancer activity is increased thanks to the fluoridation of the A ring. See also *Anti-cancer Drug Design*, (2001), 16, 27-36, for the substitution with chlorine in position 12.

The problem of the hydrosolubility of the homocamptothecins is addressed in U.S. Pat. No. 6,291,676, University of Kentucky, published on Sep. 18, 2001 with various substitutions of the (poly)alkylamine type in position 7.

However much in the design of new drugs various problems are encountered of a physicochemical nature, such as the stability of the molecule in plasma or its hydrosolubility for formulatory purposes, there is a constant search for a better therapeutic index.

SUMMARY OF THE INVENTION

It has now surprisingly been found that substituted 7-oxime camptothecins, with a modified lactone ring, are endowed with substantial anticancer activity and are stable in plasma. These compounds have a better therapeutic index.

The objects of the invention described herein are therefore compounds of general formula (I) and (II):

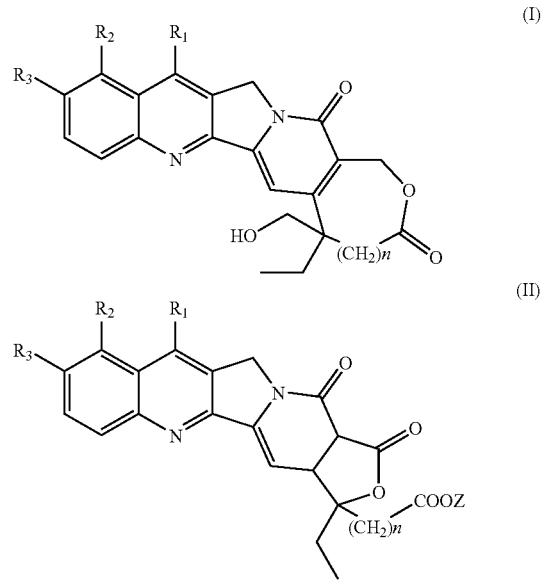

where:

$R_1$ is hydrogen or a —C($R_5$)=N—O—$R_4$ group, in which $R_4$ is hydrogen or a straight or branched $C_1$-$C_5$ alkyl or $C_1$-$C_5$ alkenyl group, or a $C_3$-$C_{10}$ cycloalkyl group, or a straight or branched ($C_3$-$C_{10}$) cycloalkyl-($C_1$-$C_5$) alkyl group, or a $C_6$-$C_{14}$ aryl group, or a straight or branched ($C_6$-$C_{14}$) aryl-($C_1$-$C_5$) alkyl group, or a heterocyclic group or a straight or branched heterocyclo-($C_1$-$C_5$) alkyl group, said heterocyclic group containing at least one heteroatom selected from an atom of nitrogen, optionally substituted with an ($C_1$-$C_5$) alkyl group, and/or an atom of oxygen and/or of sulphur; said alkyl, alkenyl, cycloalkyl, cycloalkyl-alkyl, aryl, aryl-alkyl, heterocyclic or heterocyclo-alkyl groups can optionally be substituted with one or more groups selected from the group consisting of: halogen, hydroxy, $C_1$-$C_5$ alkyl, $C_1$-$C_5$ alkoxy, phenyl, cyano, nitro, and —$NR_6R_7$, where $R_6$ and $R_7$, which may be the same or different, are hydrogen, straight or branched ($C_1$-$C_5$) alkyl, the —COOH group or one of its pharmaceutically acceptable esters; or the —$CONR_8R_9$ group, where $R_8$ and $R_9$, which may be the same or different, are hydrogen, straight or branched ($C_1$-$C_5$) alkyl; or $R_4$ is a ($C_6$-$C_{10}$) aroyl or ($C_6$-$C_{10}$) arylsulphonyl residue, optionally substituted with one or more groups selected from: halogen, hydroxy, straight or branched $C_1$-$C_5$ alkyl, straight or branched $C_1$-$C_5$ alkoxy, phenyl, cyano, nitro, —$NR_{10}R_{11}$, where $R_{10}$ and $R_{11}$, which may be the same or different, are hydrogen, straight or branched $C_1$-$C_5$ alkyl; or: $R_4$ is a polyaminoalkyl residue; or $R_4$ is a glycosyl residue;

$R_5$ is hydrogen, straight or branched $C_1$-$C_5$ alkyl, straight or branched $C_1$-$C_5$ alkenyl, $C_3$-$C_{10}$ cycloalkyl, straight or branched ($C_3$-$C_{10}$) cycloalkyl-($C_1$-$C_5$) alkyl, $C_6$-$C_{14}$ aryl, straight or branched ($C_6$-$C_{14}$) aryl-($C_1$-$C_5$) alkyl;

$R_2$ and $R_3$, which may be the same or different, are hydrogen, hydroxy, straight or branched $C_1$-$C_5$ alkoxy;

n=1 or 2,

Z is selected from hydrogen, straight or branched $C_1$-$C_4$ alkyl;

the $N_1$-oxides, the racemic mixtures, their individual enantiomers, their individual diastereoisomers, their mixtures, and their pharmaceutically acceptable salts, with the proviso that, in formula (I), $R_1$, $R_2$ and $R_3$ cannot be simultaneously hydrogen.

The present invention includes the use of compounds of the above-mentioned formulae (I) and (II) as active ingredients for medicaments, particularly for medicaments which are useful as topoisomerase I inhibitors. Among the therapeutic applications deriving from topoisomerase I inhibition we should mention the treatment of tumours and parasitic or viral infections.

The present invention includes pharmaceutical compositions containing compounds of formula (I) and/or formula (II) as active ingredients, in admixture with pharmaceutically acceptable vehicles and excipients.

The present invention also includes the processes for the preparation of compounds of formula (I) and (II), and the key intermediate products.

DETAILED DESCRIPTION OF THE INVENTION

Within the framework of the present invention, examples of the straight or branched $C_1$-$C_5$ alkyl group, are understood to include methyl, ethyl, propyl, butyl, pentyl and their possible isomers, such as, for example, isopropyl, isobutyl, and ter-butyl.

Examples of the branched or straight $C_1$-$C_5$ alkenyl group are methylidene, ethylidene, vinyl, allyl, propargyl, butylene, and pentylene, where the double carbon-carbon bond may be situated in the various possible positions of the alkylene ring, which can also be branched in the context of the isomery allowed.

Examples of the $C_3$-$C_{10}$ cycloalkyl group are cyclopropyl, cyclobutyl, cyclopentyl, cyclohexyl, cyclooctyl, and polycyclic groups, such as, for example, adamantyl.

Examples of the straight or branched ($C_3$-$C_{10}$) cycloalkyl-($C_1$-$C_5$) alkyl group are cyclopropylmethyl, 2-cyclopropylethyl, 1-cyclopropylethyl, 3-cyclopropylpropyl, 2-cyclopropylpropyl, 1-cyclopropylpropyl, cyclobutylmethyl, 2-cyclobutylethyl, 1-cyclobutylethyl, 3-cyclobutylpropyl, 2-cyclobutylpropyl, 1-cyclobutylpropyl, cyclohexylmethyl, 2-cyclohexylethyl, 1-cyclohexylethyl, 3-cyclohexylpropyl, 2-cyclohexylpropyl, 1-cyclohexylpropyl, 5-cyclohexylpentyl, 3-cyclohexylpentyl, 3-methyl-2-cyclohexylbutyl, 1-adamantylethyl, 2-adamantylethyl, adamantylmethyl.

Examples of the straight or branched ($C_6$-$C_{14}$) aryl or ($C_6$-$C_{14}$) aryl-($C_1$-$C_5$) alkyl group are phenyl, 1- or 2-naphthyl, anthracenyl, benzyl, 2-phenylethyl, 1-phenylethyl, 3-phenylpropyl, 2-anthracenylpropyl, 1-anthracenylpropyl, naphthylmethyl, 2-naphthylethyl, 1-naphthylethyl, 3-naphthyl-propyl, 2-naphthylpropyl, 1-naphthylpropyl, cyclohexylmethyl, 5-phenylpentyl, 3-phenylpentyl, 3-methyl-2-phenylbutyl.

Examples of the straight or branched heterocyclic or heterocyclo-($C_1$-$C_5$) alkyl group are thienyl, quinolyl, pyridyl, N-methylpiperidinyl, 5-tetrazolyl, 2-(4,5-dihydroxazolyl), 1,2,4-oxadiazolidin-3-yl-5-one, purine and pyrimidine bases, e.g. uracyl, optionally substituted as indicated in the general definitions above.

Examples of the ($C_6$-$C_{10}$) aroyl groups are benzoyl and naphthoyl.

Examples of the ($C_6$-$C_{10}$) arylsulphonyl groups are tosyl and benzoylsulphonyl.

What is meant by halogen is fluorine, chlorine, bromine and iodine.

Examples of substituted groups are pentafluorophenyl, 4-phenyl-benzyl, 2,4-difluorobenzyl, 4-aminobutyl, 4-hydroxybutyl, dimethyl-aminoethyl, p-nitrobenzoyl, p-cyanobenzoyl.

An example of the polyaminoalkyl residue is —$(CH_2)_m$—$NR_{12}$—$(CH_2)_p$—$NR_{13}$—$(CH_2)_q$—$NH_2$, where m, p and q are whole numbers from 2 to 6 inclusive and $R_{12}$ and $R_{13}$ are a straight or branched ($C_1$-$C_5$) alkyl group, for example 4-aminobutyl-2-aminoethyl, 3-amino-propyl-4-aminobutyl, 3-aminopropyl-4-aminobutyl-3-aminopropyl.

Examples of the glycosyl residue are 6-D-galactosyl and 6-D-glucosyl.

Examples of pharmaceutically acceptable salts are, in the case of atoms of nitrogen of a basic nature, salts with pharmaceutically acceptable acids, both inorganic and organic, such as, for example, hydrochloric acid, sulphuric acid, acetic acid, or, in the case of an acid group, such as carboxyl, salts with pharmaceutically acceptable bases, such as, for example, alkaline and alkaline-hearth hydroxides, ammonium hydroxide, and amines, including heterocyclic amines.

One first group of preferred compounds comprises formula (I) compounds in which the lactone ring is 7- or 8-membered, particularly 7-membered.

A second group of preferred compounds comprises formula (II) compounds in which the lactone ring is 5-membered.

In the context of the above-mentioned two preferred groups, those preferred are the formula (I) compounds, in which $R_4$ is different from hydrogen, and particularly a straight or branched $C_1$-$C_5$ alkyl or $C_1$-$C_5$ alkenyl or $C_3$-$C_{10}$ cycloalkyl, or ($C_3$-$C_{10}$) cycloalkyl-($C_1$-$C_5$) alkyl group, or a straight or branched $C_6$-$C_{14}$ aryl, or ($C_6$-$C_{14}$) aryl-($C_1$-$C_5$) alkyl group, or a straight or branched heterocyclic or heterocyclo-($C_1$-$C_5$) alkyl group, said heterocyclic group containing at least one heteroatom selected from an atom of nitrogen, optionally substituted with a ($C_1$-$C_5$) alkyl group, and/or of oxygen and/or of sulphur; said alkyl, alkenyl, cycloalkyl, aryl, aryl-alkyl, heterocycle or heterocyclo-alkyl groups, may be substituted with one or more groups selected from: halogen, hydroxy, $C_1$-$C_5$ alkyl, $C_1$-$C_5$ alkoxy, phenyl, cyano, nitro, —$NR_6R_7$, where $R_6$ and $R_7$, which may be the same or different, are straight or branched ($C_1$-$C_5$) alkyl; the —COOH group or one of its pharmaceutically acceptable esters; or the —$CONR_8R_9$ group, where $R_8$ and $R_9$, which may be the same or different, are hydrogen, straight or branched ($C_1$-$C_5$) alkyl, according to the definitions outlined above as examples.

An initial group of particularly preferred compounds consists of formula (I) compounds, with a 7-membered lactone ring, and, among these, particularly:
R,S-7-methoxyiminomethyl-homocamptothecin;
R,S-7-ethoxyiminomethyl-homocamptothecin;
R,S-7-isopropoxyiminomethyl-homocamptothecin;
R,S-7-(2-methylbutoxy)iminomethyl-homocamptothecin;
R,S-7-(1-t-butoxy)iminomethyl-homocamptothecin (ST2127);
R,S-7-(4-hydroxybutoxy)iminomethyl-homocamptothecin;
R,S-7- triphenylmethoxyiminomethyl-homocamptothecin;
R,S-7-carboxymethoxyiminomethyl-homocamptothecin;
R,S-7-aminoethoxyiminomethyl-homocamptothecin;
R,S-7-(N,N-dimethylaminoethoxy)iminomethyl-homocamptothecin;
R,S-7-allyloxyiminomethyl-homocamptothecin;
R,S-7-cyclohexyloxyiminomethyl-homocamptothecin;
R,S-7-cyclohexylmethoxyiminomethyl-homocamptothecin;
R,S-7-cyclooctyloxyiminomethyl-homocamptothecin;
R,S-7-cyclooctylmethoxyiminomethyl-homocamptothecin;
R,S-7-benzyloxyiminomethyl-homocamptothecin (ST2143);
R,S-7-(benzyloxy)iminophenylmethyl-homocamptothecin;
R,S-7-(1-benzyloxy)iminoethyl-homocamptothecin;
R,S-7-(1-t-butoxy)iminoethyl-homocamptothecin;
R,S-7-p-nitrobenzyloxyiminomethyl-homocamptothecin;
R,S-7-p-methylbenzyloxyiminomethyl-homocamptothecin;
R,S-7-pentafluorobenzyloxyiminomethyl-homocamptothecin;
R,S-7-p-phenylbenzyloxyiminomethyl-homocamptothecin;
R,S-7-(2,4-difluorobenzylmethoxy)iminomethyl-homocamptothecin;
R,S-7-(4-t-butylphenylmethoxy)iminomethyl-homocamptothecin;
R,S-7-(1-adamantyloxy)iminomethyl-homocamptothecin;
R,S-7-(1-adamantylmethoxy)iminomethyl-homocamptothecin;
R,S-7-(2-naphthalenyloxy)iminomethyl-homocamptothecin;
R,S-7-(9-anthracenylmethoxy)iminomethyl-homo-camptothecin;
R,S-7-(6-uracyl)methoxyiminomethyl-homocamptothecin;
R,S-7-(4-pyridil)methoxyiminomethyl-homocamptothecin;
R,S-7-(2-thienyl)methoxyiminomethyl-homocamptothecin;
R,S-7-[(N-methyl)-3-piperidinyl]methoxyiminomethyl-homocamptothecin;
R,S-7-hydroxyiminophenylmethyl-homocamptothecin.

Among these compounds, those most preferred are R,S-7-(1-t-butoxy)iminomethyl-homocamptothecin (ST2127) and R,S-7-benzyl-oxyiminomethyl-homocamptothecin (ST2143).

A second group of particularly preferred compounds consists of formula (II) compounds, with a 5-membered lactone ring and with the same meanings of $R_1$ as in the preceding group.

Among these compounds, those which are most preferred are {10-[(E)-(ter-butoxyimino)methyl]-3-ethyl-1,13-dioxo-11,13-dihydro-1H,3H-furo[3',4':6,7]indolizino[1,2-b]quinolin-3-yl}acetic acid (ST2196), (10-{(E)-[(benzyloxy)imino]methyl}-3-ethyl-1,13-dioxo-11,13-dihydro-1H,3H-furo[3',4':6,7]indolizino[1,2-b]quinolin-3-yl)acetic acid (ST2285) and (3-ethyl-1,13-dioxo-11,13-dihydro-1H,3H-furo[3',4':6,7]indolizino [1,2-b]quinolin-3-yl)acetic acid (ST2085).

In a first preferred embodiment of the invention, compounds of general formula (I) are envisaged, where the lactone ring is 7- or 8-membered. In a second preferred embodiment of the invention, compounds of general formula (II) are envisaged, where the lactone ring is 5-membered.

The formula (I) compounds can be prepared with the process described here below and exemplified for the preferred compounds according to the present invention.

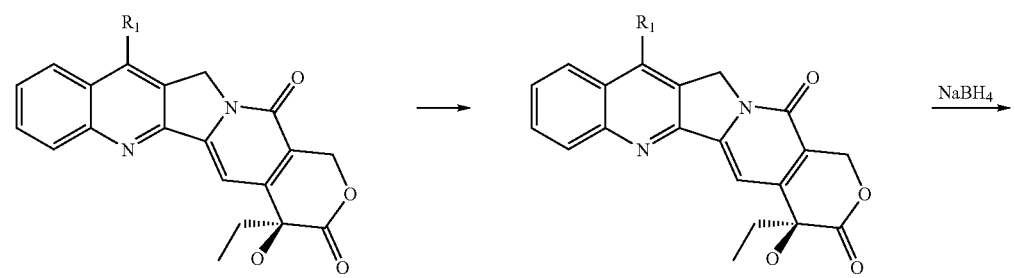

S-comptolocina

1a $R_1$ = CH(OCH$_3$)$_3$
1b $R_1$ = H

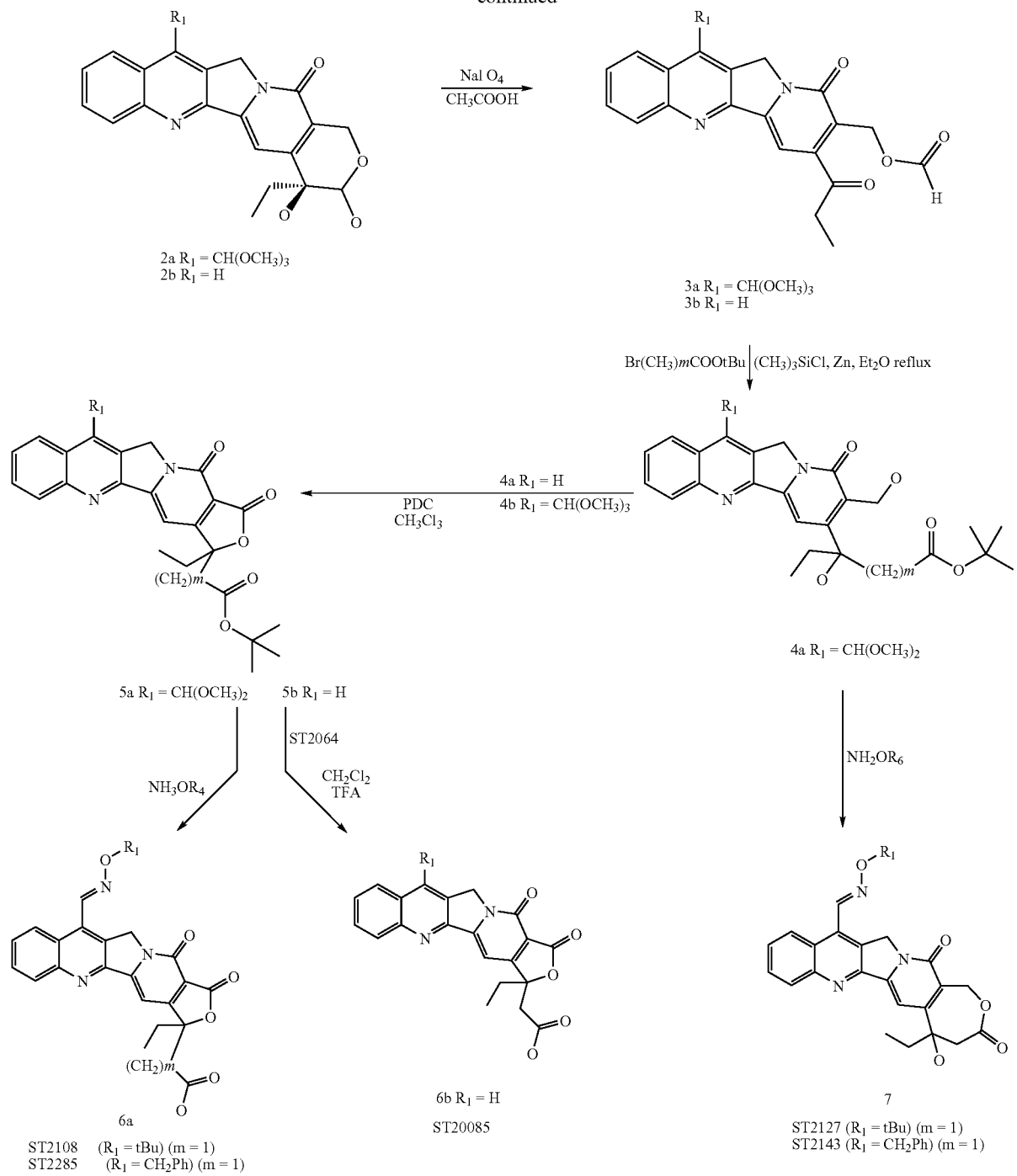

It is quite obvious to the person with ordinary experience in the field that the process scheme applies to all the compounds covered by formulae (I) and (II), since the method for obtaining the two classes of compounds with the 7-/8-membered lactone ring, on the one hand, and the 5-membered ring, on the other, is fully described. The preparation of the various compounds covered by the two formulae differs in the substituent in position 7.

This preparation is described amply and completely in the above-mentioned EP 104977.

As regards the formula (I) and (II) compounds in which $R_1$ is hydrogen, the starting compound is camptothecin, optionally substituted in positions 8 and 9 according to the meanings of the $R_2$ and $R_3$ groups envisaged above.

In the case of formula (I) and (II) compounds in which $R_1$ is other than hydrogen, the functionalisation of position 7 to obtain the final compound cannot happen before the modification of the original lactone ring of camptothecin, both in the sense of its amplification to 7 or 8 members and in the sense of its restriction to 5 members. For this purpose, it has proved necessary to find a suitable intermediate product for the synthesis pathway envisaged. This key intermediate is 7-(dialkoxymethyl)camptothecin. This new compound is an additional object of the present invention. Among these, the preferred compound is 7-(dimethoxymethyl)camptothecin. The camptothecin is reacted with the desired alcohol, which can also be used as a reaction medium, in the presence of a mineral acid, such as, for example, sulphuric acid, and a suitable oxidising system, such as iron sulphate/hydrogen peroxide, then a further oxidising agent, such as manganese dioxide to obtain 7-(dialkoxymethyl)camptothecin.

Camptothecin, or its 7-(dialkoxymethyl)-derivative, are subjected to selective reduction of the carbonyl in position 19, to obtain the corresponding 19,20-dihydroxy derivative. The reduction is carried out in the presence of a reducing agent, for example, mixed hydrides of Al or B and exemplified in the scheme by sodium borohydride, from 1 to 10 equivalents in the presence of an alcoholic solvent for a period of time ranging from 1 to 16 h at a temperature ranging from room temperature to 50° C. The solvent is subsequently evaporated and the crude product is used in the subsequent step, where the E ring, in the form of the 19,20-dihydroxy derivative, is subjected to opening with from 1 to 10 equivalents of an oxidising agent, such as, for example, periodate or lead acetate. The reaction is conveniently carried out in an organic solvent, such as, for example, toluene, methylene chloride or acetic acid, for a time period ranging from 1 to 24 h, at a temperature ranging from room temperature to 50° C. The solvent is removed in vacuo and the product is finally purified by chromatography or some other equivalent means. The intermediate product thus obtained is in turn dissolved in a suitable solvent medium, preferably a mixture of solvents, and then subjected to the well known Reformatsky reaction, in which the ω-bromocarboxylic acid is suitably selected as a function of the n value envisaged in formula (I) or (II). At this point, in the context of the embodiment of the present invention relating to formula (I) compounds, to the product of the Reformatsky reaction, dissolved in a suitable mixture of solvents, such as, for example, methylene chloride, acetic acid, and dimethyl formamide, optionally in the presence of an acid (for example, trifluoroacetic acid or a Lewis acid) and of a condensing agent (dicyclohexylcarbodiimide—DCC—or 1-(3-dimethylaminopropyl)-3-ethylcarbodiimide hydrochloride) or a dehydrating agent (for example, sodium or magnesium sulphate, or molecular sieves), are added from 1 to 10 equivalents of a suitable hydroxylamine $NH_2OR_4$, also in the form of a salt, where $R_4$ has the meanings described above for times ranging from 1 to 24 h, at a temperature ranging from room temperature to the boiling point of the solvent, to obtain the final formula (I) compound. The final product is isolated by removal of the solvent and final purification, for example, by chromatography. Alternatively, in the context of the second preferred embodiment of the invention, that is to say of formula (II) compounds in which the lactone ring is 5-membered, the product of the Reformatsky reaction, after being dissolved in a mixture of organic solvents, such as methylene chloride, acetic acid, and acetonitrile, is treated with from 1 to 10 equivalents of an oxidising agent (for example, chromic acid, pyridinium dichromate—PDC—manganese oxide, $Na_2RuO_4$) at a temperature ranging from 0° C. to the boiling point of the solvent, for a time period ranging from 30 minutes to 24 h. The solvent is then removed in vacuo and the product purified by chromatography. The resulting compound is dissolved in a suitable organic solvent, such as, for example, methylene chloride) or an aqueous solvent and subjected to acid hydrolysis with an organic or inorganic acid, such as trifluoroacetic acid, hydrochloric acid, or perchloric acid) for a time period ranging from 1 to 24 h at a temperature ranging from 0° C. to the boiling point of the solvent. The latter is then removed and the product isolated by crystallisation. If desired, the product is finally reacted with the hydroxylamine $NH_2OR_4$ as seen above. If formula (II) compounds, where Z is hydrogen, are desired, the compound obtained by the process described here above will be subjected to suitable treatment to release the carboxylic function according to conventional ester hydrolysis methods with which the experts in the field are fully familiar.

The reaction with the hydroxylamine $NH_2OR_4$ is amply described in the above-mentioned patent EP 1044977, as is the preparation of possible N-oxides.

Pharmaceutically acceptable salts are obtained with conventional methods reported in the literature and do not require any further description.

The compounds described in the present invention are topoisomerase I inhibitors and therefore are useful as medicaments, particularly for the treatment of diseases that benefit from the inhibition of said topoisomerase. In particular, the compounds according to the present invention display antiproliferative activity and are therefore used on account of their therapeutic activity and possess physico-chemical properties that make them suitable for formulation in pharmaceutical compositions.

The pharmaceutical compositions contain at least one formula (I) and/or formula (II) compound as an active ingredient, in an amount such as to produce a significant therapeutic effect. The compositions covered by the present invention are wholly conventional and are obtained with methods which are common practice in the pharmaceutical industry. According to the administration route opted for, the compositions will be in solid or liquid form, suitable for oral, parenteral, or intravenous administration. The compositions according to the present invention contain, along with the active ingredient, at least one pharmaceutically acceptable vehicle or excipient. Particularly useful may be formulation coadjuvants, such as, for example, solubilisers, dispersant agents, suspension agents and emulsifiers.

The formula (I) compounds can also be used in combination with other active ingredients, such as, for example, other anticancer drugs or other drugs with antiparasitic or antiviral activity, both in separate and in single dosage forms.

The compounds according to the present invention are useful as medicaments with anticancer activity, for example, in lung cancers, such as non-microcytoma lung cancer, or in colorectal or prostate tumours or gliomas.

The cytotoxic activity of the compounds according to the present invention has been assayed in cell systems of human tumour cells, using the antiproliferative activity test as the method of evaluating the cytotoxic potential.

The cell line used is a non-microcytoma pulmonary adenocarcinoma called NCI H460, belonging to the NSCLC (non small cell lung cancer) class.

Anticancer Activity

To evaluate the effect of the compounds according to the present invention, their cytotoxocity against the non-microcytoma lung cancer cell line (NCI-H460) was evaluated. Cells from the American Type Culture Collection (ATCC) were maintained in culture in RPMI 1640 (GIBCO) containing 10% foetal calf serum and gentamicin sulphate at a concentration of 50 g/ml.

The cells were seeded in a volume of 250 µl in 96-well plates and incubated for 24 h at 37° C. The next day the study compounds were added at scalar concentrations from 1 µM to 0.004 µM, and the cells were incubated for another 2 h at 37° C. in a humidified atmosphere containing 5% $CO_2$. The cells were washed 3 times, overturning the plates each time and adding PBS. 200 µl/well of RPMI 1640 medium containing 10% FCS were added and the plates were incubated at 37° C. for a further 72 h. On day 5, the growth medium was removed by overturning the plates, and 200 µl/well of PBS and 50 µl of 80% cold TCA were added. The plates were then incubated in ice for at least 1 h. The TCA was removed by overturning; the plates were washed 3 times by immersion in distilled water and dried first on blotting paper and then under a hot air jet. 200 µl of 0.4% sulforodamine B in 1% acetic acid were added to all wells. The plates were incubated at room temperature for a further 30 minutes. The sulforodamine B was removed by overturning; the plates were washed by immersion 3 times in 1% acetic acid and then dried first on blotting paper and then with a jet of hot air. 200 µl of Tris base 10 mM were added to all wells and the plates were subjected to stirring for at least 20 minutes. The optical density was measured using a Multiskan spectrophotometer at 540 nm.

Table 1 presents the $IC_{50}$ values, that is to say the concentration capable of inhibiting 50% of cell survival, for each compound examined, processed using ALLFIT software.

TABLE 1

| Product | NCI-H460 $IC_{50}$ (µM) |
| --- | --- |
| ST2084 | >1 |
| ST2085 | >1 |
| ST2127 | 0.026 |
| ST2143 | 0.007 |
| ST2196 | >1 |
| ST2285 | >1 |

The following examples further illustrate the invention, referring to the scheme indicated above.

Preparation 1

Synthesis of 7-(dimethoxymethyl)camptothecin (ST2337)

To a suspension of 1.53 g (4.4 mmol) of camptothecin in 92 ml of methanol, cooled with an ice bath under stirring, were added slowly 9.2 ml of $H_2SO_4$ 96%, keeping the temperature of the mixture below 50° C. The suspension thus obtained was heated to reflux temperature; on reaching 50° C., 46 mg of $FeSO_4 \cdot 7H_2O$ were added and then 3 ml of $H_2O_2$ 30% dropwise, keeping the reaction at reflux temperature. The reaction was stirred for 2 hours, checking for disappearance of the starting product by TLC. On completion of the reaction, the suspension was cooled to 25° C. and 2.8 ml of $MnO_2$ were added; the mixture was stirred for 2 hours, checking for disappearance of the intermediate product by TLC. The suspension was then filtered through a layer of Celite placed on a Gooch filter. The filtered solution was concentrated to 25 ml and then poured into a solution of $NaHCO_3$ in water so as to obtain a solution at pH 6. The precipitate was filtered and purified on a silica gel chromatography column (eluents: $CH_2Cl_2$/MEOH 99/1). 1.02 g (2.42 mmol, 55%) of product were obtained as a yellow solid.

$C_{23}H_{22}N_2O_6$ (422,4); m.p. (decomp.)=201° C.; $R_f$=0.5 ($CH_2Cl_2$/MeOH 92/8). MS (IS): $[M+Na]^+$=445; $[M-1]^-$=421. Elemental analysis: calculated: C, 65.40; H, 5.21; N, 6.64. found: C, 65.37; H, 5.22; N, 6.67. $^1$H NMR ($CDCl_3$) δ=1.00-1.06,(t, 3H, $CH_3$), 1.82-1.97 (m, 2H, $CH_2$), 3.40 (s, 3H, $CH_3$), 3.43 (s, 3H, $CH_3$), 5.28-(5.33-5.72)-5.78 (dd, 2H, $CH_2$), 5.47 (s, 2H, $CH_2$), 6.24 (s, 1H, CH), 7.62-7.70 (m, 2H, $CH+CH_{Ar}$), 7.78-7.84 (t, 1H, $CH_{Ar}$), 8.23-8.33 (m, 2H, $CH_{Ar}$). $^{13}$C NMR ($CDCl_3$) δ=8.0; 31.9; 52.1; 52.9; 53.2; 66.7; 72.9; 98.1; 100.5; 119.0; 124.6; 125.9; 127.8; 128.4; 130.5; 138.4; 146.2; 149.4; 150.2; 152.7; 158.0; 174.1.

Preparation 2

Synthesis of Intermediate Product 2a

To a solution of 2.12 g (56 mmol, 3.3 eq) of $NaBH_4$ in 70 mL of MeOH were added 7.2 g (17 mmol) of 7-dimethylacetal camptothecin (1a); the mixture thus obtained was stirred at room temperature for 1 h. At the end of this operation acetone was added to destroy the $NaBH_4$ in excess and the solution was brought to dryness. The crude reaction product was purified by flash chromatography on silica gel (eluent gradient $CH_2Cl_2$/MeOH 92/8 $CH_2Cl_2$/MeOH 7/3) to yield 3.7 g (8.7 mmol, 51%) of product as a yellow solid.

$C_{23}H_{24}N_2O_6$ (424.5); $R_f$=0.41 (1st isomer), 0.35 (2nd isomer) ($CH_2Cl_2$/MeOH 92/8). MS (IS): $[MH]^+$=425; $[M+Na]^+$=447; $[M-1]^-$=423. Elemental analysis: calculated: C, 65.09; H, 5.66; N, 6.60. found C, 65.12; H, 5.68; N, 6.57. $^1$H NMR (DMSO-d6) δ=0.84-0.90 (t, 3H, $CH_3$), 1.65-1.73 (m, 2H, $CH_2$), 3.38 (s, 6H, $CH_3$), 4.43-(4.50-4.57) 4.64 (dd, 2H, $CH_2$), 4.98 (s, 1H, CH), 5.28 (s, 2H, $CH_2$), 6.32 (s, 1H, CH), 7.38 (s, 1H, CH), 7.66-7.73 (t, 1H, $CH_{Ar}$), 7.8-7.88 (t, 1H, $CH_{Ar}$), 8.14-8.17 (d, 1H, $CH_{Ar}$), 8.3-8.33 (d, 1H, $CH_{Ar}$). $^{13}$C NMR (DMSO-d6) δ=7.6; 32.4; 50.7; 53.1; 53.5; 58.2; 70.1; 78.3; 92.5; 96.0; 98.4; 100.3; 123.1; 124.9; 127.3; 129.4; 129.9; 137.6; 142.3; 148.3; 150.1; 153.1; 157.1.

Preparation 3

Synthesis of Intermediate Product 3a

To a solution of 5.52 g (13 mmol) of 2a in 100 ml of $CH_3COOH$ were added 4.17 g of $NaIO_4$ (19.5 mmol, 1.5 eq.). The mixture was stirred at room temperature for 16 h; at the end of this operation, the solution was concentrated and diluted with $CH_2Cl_2$, then extracted with $NaHCO_3$ to neutral pH. The organic phase was dried on $Na_2SO_4$ and evaporated to dryness. Purification was performed by flash chromatography on silica gel (eluents: $CH_2Cl_2$/MeOH 98/2). 3.58 g (8.48 mmol, 65%) of product were obtained as a yellow solid.

$C_{23}H_{22}N_2O_6$ (422.4); m.p. (decomp.)=150° C.; $R_f$=0.6 ($CH_2Cl_2$/MeOH 95/5). Elemental analysis: calculated: C, 65.40; H, 5.21; N, 6.64. found C, 65.39; H, 5.23; N, 6.61. MS (IS): $[MH^+]$=423; $[M+Na]^+$=445. $^1$H NMR (DMSO-d6) δ=1.07-1.2 (t, 3H, $CH_3$), 2.96-3.3 (m, 2H, $CH_2$), 3.37 (s, 6H, $CH_3$), 5.12 (s, 2H, $CH_2$), 5.18 (s, 2H, $CH_2$), 6.37 (s, 1H, CH), 7.38 (s, 1H, CH), 7.73-7.79 (t, 1H, $CH_{Ar}$), 7.86-7.92 (t, 1H, $CH_{Ar}$), 8.16-8.20 (d, 1H, $CH_{Ar}$), 8.27 (s, 1H, CH), 8.33-8.37 (d, 1H, $CH_{Ar}$).

Preparation 4

Synthesis of Intermediate Product 4a

A suspension of 7.6 g (116 mmol) of zinc in 60 ml of anhydrous (distilled) $Et_2O$, maintained under argon and under stirring, was activated by dropwise addition of 0.87 ml (6.8 mmol) of chlorotrimethylsilane. The suspension was stirred for 15 minutes, and then brought to reflux temperature. After removing the oil bath, 17.5 ml (118 mmol) of tert-butylbromoacetate were added dropwise at a rate such as to maintain the mixture at reflux temperature: a colourless solution was obtained. After resulming heating, the reaction was maintained at reflux temperature for 1 h; at the end of this period, a suspension of 2.3 g (5.45 mmol) of 3a in 45 ml of anhydrous (distilled) THF was added, keeping the reaction under argon. The mixture thus obtained was stirred at reflux temperature. After 1 h the mixture, which had become a yellow solution, was spent with 200 ml of saturated ammonium chloride solution and extracted with $CH_2Cl_2$; the organic phase was dried on $Na_2SO_4$, the solvent was evaporated and the crude product purified by flash chromatography on silica gel (eluent gradient $CH_2Cl_2$ $CH_2Cl_2$/MeOH 98/2). 1.6 g (3.14 mmol, 58%) of product were obtained as a yellow solid.

$C_{28}H_{34}N_2O_7$ (510.6); m.p. (decomp.)=190° C.; $R_f$=0.3 ($CH_2Cl_2$/MeOH 98/2); $R_f$=0.5 ($CH_2Cl_2$/MeOH 95/5). MS (IS): $[MH]^+$=511; $[M+Na]^+$=533; $[M-1]^-$=509. Elemental analysis: calculated: C, 65.88; H, 6.67; N, 5.49. found C, 66.00; H, 6.68; N, 5.47. $^1H$ NMR ($CDCl_3$) $\delta$=0.90-0.95 (t, 3H, $CH_3$), 1.38 (s, 9H, t-Bu), 1,93-2,08 (m, 2H, $CH_2$), 2,8-(2,86-3,08)3,14 (dd, 2H, $CH_2$), 3.4 (s, 6H, $CH_3$), 5.06-(5.01-5.13)-5.17 (d, 2H, $CH_2$), 5.47 (s, 2H, $CH_2$), 6.24 (s, 1H, CH), 7.47 (s, 1H, CH), 7.64-7.69 (t, 1H, $CH_{Ar}$), 7.79-7.84 (t, 1H, $CH_{Ar}$), 8.23-8.32 (m, 2H, $CH_{Ar}$). $^{13}C$ NMR ($CDCl_3$) $\delta$=8.4; 28.2; 34.8; 45.5; 52.0; 53.0; 53.1; 59.1; 82.7; 100.6; 101.0; 124.8; 125.9; 128.0; 128.2; 130.0; 130.4; 130.5; 138.6; 142.4; 148.9; 152.9; 155.2; 162.6; 172.6.

Preparation 5

Synthesis of Intermediate Product 5a 383 mg (0.75 mmol) of 4a and 564 mg (1.5 mmol, 2 eq.) of PDC were suspended in 4 ml of anhydrous $CH_2Cl_2$; the mixture thus obtained was placed under stirring at room temperature. After 16 h the solvent was removed by evaporation and the crude product thus obtained was purified by chromatography on a silica column (eluents: $CH2Cl_2$/MeOH 99/1) yielding 280 mg (0.55 mmol, 74%) of product.

$C_{28}H_{30}N_2O_7$ (506.5); m.p. (decomp.)=210° C.; $R_f$=0.64 ($CH_2Cl_2$/MeOH 95/5) MS (IS): $[M+Na]^+$=529; $[M-1]^-$=505. Elemental analysis: calculated: C, 66.40; H, 5.93; N, 5.53. found C, 66.42; H, 5.96; N, 5.53. $^1H$ NMR ($CDCl_3$) $\delta$=0.83-0.90 (t, 3H, $CH_3$), 1.33 (s, 9H, $CH_3$), 1.97-(2.06-2.15) 2.24 (double multiplet, 2H, $CH_2$), 2.90-(2.95-3.00) 3.05 (dd, 2H, $CH_2$), 3.42 (s, 6H, $CH_3$), 5.58 (s, 2H, $CH_2$), 6.28 (s, 1H, CH), 7.39 (s, 1H, CH), 7.68-7.76 (t, 1H, $CH_{Ar}$), 7.82-7.88 (t, 1H, $CH_{Ar}$), 8.23-8.27 (d, 1H, $CH_{Ar}$), 8.33-8.37 (d, 1H, $CH_{Ar}$). $^{13}C$ NMR ($CDCl1_3$) $\delta$=7.6; 28.1; 31.6; 43.8; 52.5; 53.; 53.2; 82.2; 85.0; 93.8; 100.5; 114.3; 124.9; 126.4; 129.1; 130.5; 130.9; 139.8; 149.4; 151.8; 152.4; 156.2; 167.0; 167.4; 169.9.

EXAMPLE 1

{10-[(E)-(ter-butoxyimino)methyl]-3-ethyl-1,13-dioxo-11,13-dihydro-1H,3H-furo[3',4':6,7]indolizino[1,2-b]quinolin-3-yl} acetic acid (ST2196)

To a solution of 71 mg (0.14 mmol) of 5a in 1.4 ml of $CH_3COOH$ were added 44 mg (0.35 mmol, 2.5 eq.) of $tBuONH_2.HCl$; the mixture thus obtained was stirred at 80° C. and sheltered from the light for 16 h. The $CH_3COOH$ was then removed by evaporation. The crude product thus obtained, kept sheltered from the light, was purified by chromatography on a silica column (eluent gradient: $CH_2Cl_2$→$CH_2Cl_2$/MeOH 85/15). 45 mg (0.09 mmol, 68%) of product were obtained.

$C_{26}H_{25}N_3O_6$ (475.5); m.p. (decomp.)=228° C.; $R_f$=0.3 ($CH_2Cl_2$/MeOH 9/1). MS (IS): $[MH]^+$=476; $[M+Na]^+$=498; $[M-1]^-$=474. Elemental analysis: calculated: C, 65.68; H, 5.26; N, 8.84. found: C, 65.70; H, 5.29; N, 8.83. $^1H$ NMR (DMSO-d6) $\delta$=0.63-0.7 (t, 3H, $CH_3$), 1.5 (s, 9H, tBu), 2.07-2.17 (m, 2H, $CH_2$), 2.97-(3.03-3.23) 3.29 (dd, 2H, $CH_2$), 5.36 (s, 2H, $CH_2$), 7.64 (s, 1H, CH), 7.73-7.79 (t, 1H, $CH_{Ar}$), 7.89-7.96 (t, 1H, $CH_{Ar}$), 8.16-8.20 (d, 1H, $CH_{Ar}$), 8.60-8.63 (d, 1H, $CH_{Ar}$), 9.30 (s, 1H, $CH_{Ar}$). $^{13}C$ NMR ($CDCl_3$) $\delta$=7.6; 27.8; 29.9; 31.2; 42.6; 53.1; 81.9; 85.2; 94.2; 114.2; 123.2; 125.8; 127.1; 129.0; 130.8; 130.9; 132.8; 142.2; 149.8; 151.7; 152.7; 156.2; 167.2; 170.1.

EXAMPLE 2

(10-{(E)-[(benzyloxy)imino]methyl}-3-ethyl-1,13-dioxo-11,13-dihydro-1H,3H-furo[3',4':6,7]indolizino[1,2-b]quinolin-3-yl)-acetic acid (ST2285)

To a solution of 102 mg (0.2 mmol) of 5a in 2 ml of $CH_3COOH$ were added 80 mg (0.5 mmol, 2.5 eq.) of $PhCH_2.ONH_2 \cdot HCl$; the solution was stirred at 80° C. and sheltered from the light for 16 h. The $CH_3COOH$ was then removed by evaporation. The crude product thus obtained, kept sheltered from the light, was purified by chromatography on a silica column (eluent gradient: $CH_2Cl_2$→$CH_2Cl_2$/MeOH 8/2). 62 mg (0.12 mmol, 61%) of product were obtained.

$C_{29}H_{23}N_3O_6$ (509.5); m.p. (decomp.)=188° C.; $R_f$=0.53 ($CH_2Cl_2$/MeOH 9/1). MS (IS): $[M+Na]^+$=532; $[M-1]^-$=508. Elemental analysis: calculated: C, 68.37; H, 4.52; N, 8.25. found: C, 68.41; H, 4.50; N, 8.27. $^1H$ NMR (DMSO-d6) $\delta$=0.64-0.70 (t, 3H, $CH_3$), 2.05-2.17 (m, 2H, $CH_2$), 2.84-(2.90-3.12) 3.18 (dd, 2H, $CH_2$), 5.2 (s, 2H, $CH_2$), 5.4 (s, 2H, $CH_2$), 7.36-7,58 (m, 5H, $CH_{Ar}$), 7.62 (s, 1H, CH), 7.72-7.78 (t, 1H, $CH_{Ar}$), 7.85-7.90 (t, 1H, $CH_{Ar}$), 8.12-8.16 (d, 1H, $CH_{Ar}$), 8.54-8.58 (d, 1H, $CH_{Ar}$), 9.32 (s, 1H, $CH_{Ar}$). $^{13}C$ NMR ($CDCl_3$) $\delta$=7.0; 30.6; 42.1; 52.6; 77.8; 84.8; 93.6; 113.5; 122.6; 125.2; 126.7; 128.2; 128.5; 128.6; 128.9; 130.2; 130.3; 131.2; 136.0; 143.2; 149.1; 151.0; 152.0; 155.6; 166.9; 169.7; 170.1.

EXAMPLE 3

R,S-7-(1-t-butoxy)iminomethyl-homocamptothecin (ST2127)

To a solution of 510 mg (1 mmol) of 4a in 10 ml of $CH_3COOH$ were added 314 mg (2.5 mmol, 2.5 eq) of $tBuO—NH_2.HCl$; the solution was maintained sheltered from the light at 80° C. for 16 h. The $CH_3COOH$ was then removed by evaporation. The crude product thus obtained, dissolved in $CH_2Cl_2$ and kept sheltered from the light, was washed with water. The organic phase was dried on $Na_2SO_4$, the solvent was evaporated and the crude product purified by chromatography on a silica column, keeping it sheltered from the light (eluents: $CH_2Cl_2$/dioxane 9/1). 160 mg (0.35 mmol, 34%) of solid yellow product were obtained.

$C_{26}H_{27}N_3O_5$ (461,5); m.p. (decomp.)=284° C.; $R_f$=0.4 ($CH_2Cl_2$/MeOH 95/5). MS (IS): $[MH]^+$=462; $[M+Na]^+$=484; $[M-1]^-$=460. Elemental analysis: calculated: C, 67.68; H, 5.86; N, 9.11. found: C, 67.65; H, 5.88; N, 9.13. $^1H$ NMR ($CDCl_3$) $\delta$=0.87-1.03 (t, 3H, $CH_3$), 1.55 (s, 9H, $CH_3$), 1.7-1.9 (broad, 1H, OH), 1.92-2.1 (m, 2H, $CH_2$), 3.26-(3.32-3.38) 3.44 (dd, 2H, $CH_2$), 5.13-(5.21-5.36) 5.44 (dd, 2H, $CH_2$), 5.35-(5.41-5.62) 5.68 (dd, 2H, $CH_2$), 7,43-7,50 (m, 2H, CH+$CH_{Ar}$), 7,60-7,65 (t, 1H, $CH_{Ar}$), 7.88-7.95 (t, 2H, CH), 8.86 (s, 1H, $CH_{Ar}$). $^{13}C$ NMR ($CDCl_3$) $\delta$=8.3; 27.9; 35.8; 42.7; 53.4; 62.4; 73.9; 82; 101.1; 122.9; 123.4;

125.1; 125.5; 128.3; 130.1; 130.4; 132.5; 142.1; 144.7; 149.0; 151.6; 156.4; 160.0; 1716.

HPLC analysis of (R,S) ST 2127 on a chiral column using a circular dichroism detector revealed the separation of the two enantiomers.

The enantiomers of (R,S) ST 2127 were isolated via HPLC by preparative chromatography on a chiral column in the following conditions:
column: (S,S)-DACH-DNB 5/100;
eluent: $CH_2Cl_2$/n-HEXANE (80/20)+1% MetOH;
flow rate: 1 ml/min;
T: 22° C.;
λ 360 nm UV detector.

The first eluted fraction with e.e. 99.46% corresponds to (+) ST2127=ST2522 to which the R configuration was attributed by analogy with the camptothecins with positive $[\alpha]D$.

$IC_{50}$=18 nM±0.2 (H460).

The second eluted fraction with e.e. 99.46% corresponds to (−) ST2127=ST2523 with $[\alpha]D$=−48.11±0.15 (c=1.17; $CHCl_3$—MetOH 4:1).

The S configuration was attributed to A ST2523 by analogy with the camptothecins with negative $[\alpha]D$.

$IC_{50}$=>200 nM (H460).

EXAMPLE 4

R,S-7-benzyloxyiminomethyl-homocamptothecin (ST2143)

To a solution of 510 mg (1 mmol) of 4a in 10 ml of $CH_3COOH$ were added 400 mg (2.5 mmol) of $PhCH_2ONH_2.HCl$; the solution was kept sheltered from the light and stirred at 80° C. for 16 h. The $CH_3COOH$ was then removed by evaporation. The crude product thus obtained was purified by chromatography on a silica column (eluents: $CH_2Cl_2$/dioxane 9/1). 223 mg of product were obtained as a yellow solid (0.45 mmol, yield 45%).

$C_{29}H_{25}N_3O_5$ (495.5); m.p. (decomp.)=263° C.; $R_f$=0.48 ($CH_2Cl_2$/MeOH 95/5). MS (IS): $[MH]^+$=496; $[M+Na]^+$= 518; $[M-1]^-$=494. Elemental analysis: calculated: C, 70.30; H, 5.05; N, 8.48. found: C, 70.33; H, 5.09; N, 8.47. $^1$H NMR ($CDCl_3$) δ=0.95-1.02 (t, 3H, $CH_3$), 1.99-2.06 (m, 2H, $CH_2$), 3,04-(3,08-3,18)3,42 (dd, 2H, $CH_2$), 5,32 (s, 2H, $CH_2$), 5.42-(5.44-5.63) 5.70 (dd+s, 4H, $CH_2$+$CH_2$), 7.33-7.56 (m, -5H, $CH_{Ar}$), 7.63-7.69 (m, 2H, CH+$CH_{Ar}$), 7.80-7.84 (t, 1H, $CH_{Ar}$), 8.16-8.22 (m, 2H, $CH_{Ar}$), 9.10 (s, 1H, CH). $^{13}$C NMR ($CDCl_3$) δ=8.4; 36.5; 42.6; 52.9; 62.2; 73.6; 78.1; 101.1; 123.0; 123.1; 125.3; 126.2; 128.3; 128.5; 128.8; 129.1; 130.3; 130.4; 131.4; 136.5; 144.0; 144.4; 149.2; 152.5; 156.4; 159.7; 172.1.

EXAMPLE 5

Ter-butyl ester of (3-ethyl-1,13-dioxo-11,13-dihydro-1H,3H-furo[3',4':6,7]indolizino[1,2-b]quinolin-3-yl)acetic acid (ST2084)

To a solution of 1 g (2.3 mmol) of 4b in 10 ml of anhydrous $CH_2Cl_2$ were added 1.73 g (4.6 mmol, 2 eq.) of PDC. The mixture was stirred at room temperature for 16 h. At the end of this period the reaction was brought to dryness and purified by flash chromatography on a silica column (eluents: $CH_2Cl_2$/MeOH 95/5). 726 mg (1.68 mmol, 73%) of product were obtained as a yellow solid.

$C_{25}H_{24}N_2O_5$ (432.5); m.p. (decomp.)=190° C.; $R_f$=0.5 ($CH_2Cl_2$/MeOH 95/5). MS (IS): $[MH]^+$=432; $[M+Na]^+$=455. Elemental analysis: calculated: C, 69.44; H, 5.56; N, 6.48. found: C, 69.46; H, 5.55; N, 6.51. $^1$H NMR ($CDCl_3$) δ=0.83-0.88 (t, 3H, $CH_3$), 1.35 (s, 9H, t-Bu), 1.95-2.27 (m(double multiplet), 2H, $CH_2$), 2.91-(2.96-3.01) 3.06 (dd, 2H, $CH_2$), 5.38 (s, 2H, $CH_2$), 7.36 (s, 1H, CH), 7.68-7.75 (t, 1H, $CH_{Ar}$), 7.83-7.90 (t, 1H, $CH_{Ar}$), 7.97-8.00 (d, 1H, $CH_{Ar}$), 8.22-8.25 (d, 1H, $CH_{Ar}$), 8.46 (s, 1H, $CH_{Ar}$). $^{13}$C NMR ($CDCl_3$) δ=7.5; 28.1; 31.6; 43.7; 50.6; 82.2; 85.2; 94.0; 114.3; 128.5; 128.9; 130.1; 131.2; 131.7; 149.3; 151.8; 153.0; 167.4; 170.2.

EXAMPLE 6

(3-ethyl-1,13-dioxo-11,13-dihydro-1H,3H-furor[3',4':6,7]indolizino[1,2-b]quinolin-3-yl)acetic acid-(ST2085)

110 mg (0.25 mmol) of EM 21/2 were dissolved in 1.5 ml of a 1:1 mixture of $CH_2Cl_2$/TFA. The mixture was stirred at room temperature for 16 h. The solvent was then evaporated dry to yield 94 mg of product as a yellow solid (0.25 mmol, quantitative yield).

$C_{21}H_{16}N_2O_5$ (376.4); m.p. (decomp.)=242° C.; $R_f$=0.25 ($CH_2Cl_2$/MeOH 95/5). MS (IS): $[MH]^+$=377; $[M+Na]^+$= 399; $[M-1]^-$=375. Elemental analysis: calculated: C, 67.02; H, 4.26; N, 7.45. found C,67.05; H, 4.28; N, 7.49. $^1$H NMR (DMSO-d6) δ=0.64-0.70 (t, 3H, $CH_3$), 2.03-2.16 (m, 2H, $CH_2$), 3.05-(3.10-3.30) 3.35 (dd, 2H, $CH_2$), 4.00-4.75 (broad, 1H, OH), 5.33 (s, 2H, $CH_2$), 7.65 (s, 1H, CH), 7.73-7.78 (t, 1H, $CH_{Ar}$), 7.84-7.90 (t, 1H, $CH_{Ar}$), 8.15-8.18 (d, 2H, $CH_{Ar}$), 8.73 (d, 1H, $CH_{Ar}$). $^{13}$C NMR ($CDCl_3$) δ=7.7; 31.2; 41.6; 51.5; 85.3; 94.5; 113.5; 129.0; 129.1; 129.4; 129.8; 131.4; 131.9; 132.6; 148.8; 152.5; 153.5; 156.0; 167.4; 170.5; 170.6.

The invention claimed is:
1. A compound of formula (II)

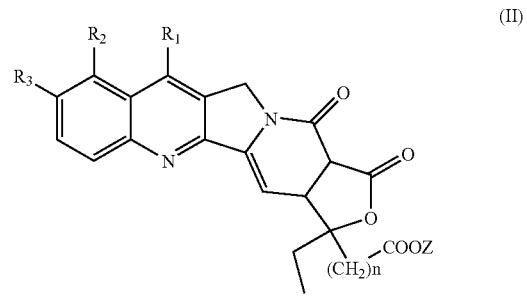

where:
R₁ is hydrogen or a —C(R₅)═N—O—R₄ group, in which R₄ is hydrogen or a straight or branched $C_1$-$C_5$ alkyl or $C_1$-$C_5$ alkenyl group, or a $C_3$-$C_{10}$ cycloalkyl group, or a straight or branched ($C_3$-$C_{10}$) cycloalkyl-($C_1$-$C_5$) alkyl group, or a $C_6$-$C_{14}$ aryl group, or a straight or branched ($C_6$-$C_{14}$) aryl-($C_1$-$C_5$) alkyl group, or a heterocyclic group or a straight or branched heterocyclo-($C_1$-$C_5$) alkyl group, said heterocyclic group containing at least one heteroatom selected from an atom of nitrogen, optionally substituted with an ($C_1$-$C_5$) alkyl group, and/or an atom of oxygen and/or of sulphur; said alkyl, alkenyl, cycloalkyl, cycloalkylalkyl, aryl, arylalkyl, heterocyclic or heterocyclo-alkyl groups can optionally be substituted with one or more groups selected from the group consisting of: halogen, hydroxy, $C_1$-$C_5$ alkyl, $C_1$-$C_5$ alkoxy, phenyl, cyano, nitro, and —$NR_6R_7$, where $R_6$ and $R_7$, which may be the same or different, are hydrogen, straight or branched ($C_1$-$C_5$) alkyl, the —COOH group or one of its pharmaceutically acceptable esters; or the —$CON_8R_9$ group, where $R_8$ and $R_9$, which may be the same or different, are hydrogen, straight or branched ($C_1$-$C_5$) alkyl; or $R_4$ is a ($C_6$-$C_{10}$) aroyl or ($C_6$-$C_{10}$) arylsulphonyl residue, optionally substituted with one or more groups selected from: halogen, hydroxy, straight or branched $C_1$-$C_5$ alkyl, straight or branched $C_1$-$C_5$ alkoxy, phenyl, cyano, nitro, —$NR_{10}R_{11}$, where $R_{10}$ and $R_{11}$, which may be the same or different, are hydrogen, straight or branched $C_1$-$C_5$ alkyl; or:

$R_4$ is a polyaminoalkyl residue; or $R_4$ is a glycosyl residue;

$R_5$ is hydrogen, straight or branched $C_1$-$C_5$ alkyl, straight or branched $C_1$-$C_5$ alkenyl, $C_3$-$C_{10}$ cycloalkyl, straight or branched ($C_3$-$C_{10}$) cycloalkyl-($C_1$-$C_5$) alkyl, $C_6$-$C_{14}$ aryl, straight or branched ($C_6$-$C_{14}$) aryl-($C_1$-$C_5$) alkyl;

$R_2$ and $R_3$, which may be the same or different, are hydrogen, hydroxy, straight or branched $C_1$-$C_5$ alkoxy;

n=1 or 2,

Z is selected from hydrogen, straight or branched $C_1$-$C_4$ alkyl;

the $N_1$-oxides, the racemic mixtures, their individual enantiomers, their individual diastereoisomers, their mixtures, and their pharmaceutically acceptable salts.

2. A compound according to claim 1, in which, in formula (II), n is 1.

3. A compound according to claim 2, selected from the group consisting of:
- {10-[(E)-(ter-butoxyimino)methyl]-3-ethyl-1,13-dioxo-11,13-dihydro-1H,3H-furo[3',4':6,7]indolizino[1,2-b]quinolin-3-yl}acetic acid,
- (10-{(E)-[(benzyloxy)imino]methyl}-3-ethyl-1,1 3-dioxo-11,13-dihydro-1H,3H-furo[3',4':6,7]indolizino[1,2-b]quinolin-3-yl)acetic acid,
- (3-ethyl-1,13-dioxo-11,13-dihydro-1H,3H-furo[3',4':6,7]indolizino[1,2-b]quinolin-3-yl)acetic acid, and
- ter-butylic ester of (3-ethyl-1,13-dioxo-11,13-dihydro-1H,3H-furo[3',4':6,7]indolizino[1,2-b]quinolin-3-yl)acetic acid.

4. A process for the preparation of a formula (II) compound according to claim 1 in which $R_1$ is hydrogen, comprising:
- a) reduction of the keto group in position 19 of the camptothecin, optionally substituted with $R_2$ and $R_3$ have the meanings as in formula (II), to yield the derivative 19,20-dihydroxy;
- b) treatment of the derivative obtained in step a) with periodate and acetic acid, to obtain the opening of the E ring;
- c) Reformatsky reaction on the derivative obtained in step b);
- d) treatment of the derivative obtained in step c) with PDC with formation of the E ring and, if so desired;
- e) transformation of the Z group to hydrogen.

5. A process for the preparation of a formula (II) compound according to claim 1 in which $R_1$ is a —$C(R_5)$=N—O—$R_4$ group, comprising:
- a) transformation of the camptothecin, optionally substituted with $R_2$ and $R_3$, to 7-(di-methoxymethyl)camptothecin;
- b) reduction of the keto group in position 19 of the 7-(di-methoxymethyl)camptothecin, optionally substituted with the envisaged meanings of $R_2$ and $R_3$, to yield a derivative 19,20-dihydroxy;
- c) treatment of the derivative obtained in step b) with periodate and acetic acid, to obtain opening of the E ring;
- d) Reformatsky reaction on the derivative obtained in step c);
- e) treatment of the derivative obtained in step d) with PDC with formation of the E ring;
- f) treatment of the compound obtained in step e) with an oxime of formula $R_4ONH_2$ and, if so desired,
- g) transformation of the Z group to hydrogen.

6. A pharmaceutical composition containing a therapeutically effective amount of at least one compound according to claim 1 in an admixture with a pharmaceutically acceptable vehicle or excipient.

* * * * *